US005782505A

United States Patent [19]
Brooks et al.

[11] Patent Number: 5,782,505
[45] Date of Patent: Jul. 21, 1998

[54] CATHETER ADAPTER ASSEMBLY

[75] Inventors: Christopher J. Brooks, New York, N.Y.; Jesse Lee Dorogusker, Palo Alto, Calif.; Keith Joseph Mc Wha, Waldwick, N.J.

[73] Assignee: Becton, Dickinson and Company, Franklin Lakes, N.J.

[21] Appl. No.: 697,759

[22] Filed: Aug. 29, 1996

[51] Int. Cl.⁶ .......................... A61M 25/00; A61M 25/18
[52] U.S. Cl. ............................ 285/175; 285/332; 604/283
[58] Field of Search .......................... 285/38, 175, 332, 285/342, 343, 346; 604/283, 326

[56] References Cited

U.S. PATENT DOCUMENTS

| 2,405,489 | 8/1946 | Brock | 285/175 X |
|---|---|---|---|
| 2,511,396 | 6/1950 | Brekke | 285/332 |
| 4,452,473 | 6/1984 | Ruschke | 604/283 X |
| 4,629,455 | 12/1986 | Kanno | 385/332 X |
| 4,690,437 | 9/1987 | Anderson | 285/343 X |
| 4,929,243 | 5/1990 | Koch et al. | 604/283 |
| 5,449,205 | 9/1995 | Silletti et al. | 285/175 X |

FOREIGN PATENT DOCUMENTS

| 2907832 | 9/1980 | Germany | 604/283 |
|---|---|---|---|
| 3515665 | 5/1986 | Germany | 604/283 |

*Primary Examiner*—John A. Ricci
*Attorney, Agent, or Firm*—Arthur D. Dawson

[57] ABSTRACT

An adapter assembly is provided for fluid communication and mechanical connection between a catheter and a syringe. The adapter assembly includes a generally tubular nose having opposed proximal and distal ends. A wall is disposed at the distal end and includes an aperture dimensioned for receiving the catheter therethrough. A compressible plug is received in the open proximal end of the nose and seats against the wall. The plug includes an axial passage for receiving the catheter. Outer portions of the plug are tapered near the proximal end. The assembly further includes a hub having opposed proximal and distal ends. The proximal end of the hub includes luer projections for threaded engagement with a luer collar of a syringe. The distal end of the hub is threadedly engageable in the opened proximal end of the nose. Internal portions of the hub adjacent the distal ends are tapered and dimensioned to gradually compress the plug into fluid-tight engagement against the catheter without generating occlusion.

12 Claims, 6 Drawing Sheets

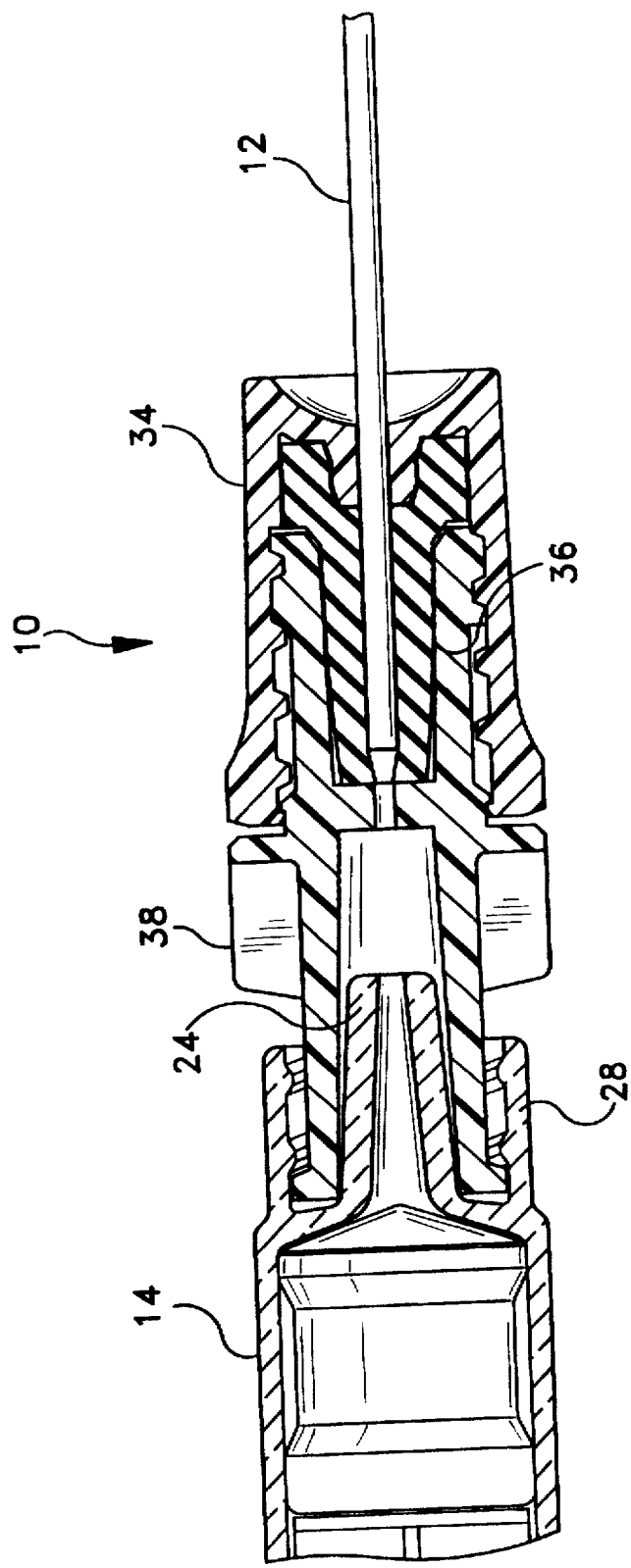

5,782,505

CATHETER ADAPTER ASSEMBLY

BACKGROUND OF THE INVETION

1. Field of the Invention

The subject invention relates to an adapter assembly for secure, fluid-tight engagement to a flexible catheter and for enabling connection of the catheter to a syringe.

2. Description of the Prior Art

A catheter is a long flexible tube that is introduced into the vascular system of a patient for administering a fluid to a patient, withdrawing a fluid from a patient or for delivering another flexible member to an area that requires treatment. The end of the catheter that is external to the patient may be connected to an adapter, which in turn may be releasably connected to a syringe or other means for generating fluid flow through the catheter.

The connection of the adapter to the catheter desirably should provide a secure mechanical connection that will prevent inadvertent separation of the catheter from the adapter. Additionally, the connection of the adapter to the catheter should be fluid-tight to prevent an unintended and potentially harmful leakage of fluid. These requirements for a catheter/adapter connection suggest that a very tight connection will meet all structural and functional demands. However, the catheter may occlude or kink if gripping forces by the adapter are too high. Thus, prior art efforts to achieve an optimum connection between the catheter and the adapter can lead to a complete failure of the connection.

A prior art catheter adapter that attempts to deal with these problems is shown, for example, in U.S. Pat. No. 5,464,400.

SUMMARY OF THE INVENTION

The adapter of the subject invention includes three components, namely, a nose, a plug and a hub.

The nose of the adapter includes a generally tubular side wall with opposed proximal and distal ends. The distal end of the tubular side wall of the nose includes a stop for positioning the nose and the plug relative to one another, as explained herein. The stop may include an inwardly directed end wall. A short tubular projection may extend proximally from the distal end wall and may be coaxially aligned within the tubular side wall of the nose. An aperture may extend through the distal end wall and the tubular projection for slidably receiving a catheter. The nose includes hub engagement means. For example, an annular locking rim may project inwardly around the open proximal end of the tubular side wall of the nose. Additionally or alternatively, the hub engagement means may include an array of internal threads.

The plug of the adapter is formed from a compressible material with opposed proximal and distal ends and a catheter engaging passage extending therebetween. The extreme distal end of the plug is engaged within the nose and adjacent the stop at the distal end of the nose. The distal end of the plug may be configured to nest with the end wall and the tubular projection in the distal end of the nose. The outer surface of the plug is conically tapered at the proximal end of the plug. A cylindrical outer surface may extend distally from the conically tapered surface.

The hub of the adapter includes proximal and distal ends and a tubular side wall extending therebetween. A plug compression cavity extends proximally into the distal end of the hub and forms a continuous conical taper with the widest portion at the extreme distal end. The hub further includes means for connection to the nose. For example the hub may include an array of external threads extending proximally from the extreme distal end. The external threads of the hub may be dimensioned for threaded engagement with internal threads in the nose. The connection means further may include an annular outwardly projecting rim dimensioned for locked snapped engagement with an inwardly projecting annular rim at the proximal end of the nose. More particularly, an outwardly projecting annular rim on the hub may be at a position for locked snapped engagement with a rim on the nose when the hub and the nose become fully threadedly engaged with one another.

Threaded engagement of the hub and the nose with one another causes the plug to deform uniformly both torsionally and compressively within the conically tapered plug compression cavity of the hub. In the fully engaged and locked condition of the adapter, there is full contact between the outside surface of the plug and the conically tapered plug compression cavity. As a result, surface pressure is evenly applied along the entire outside surface of the plug. This pressure urges the plug into gripping engagement with the catheter without causing occlusion or kinking of the catheter within the adapter.

BRIEF DESCRIPTION OF THE DRAWINGS

FIG. 7 is a cross-sectional view similar to FIG. 6, but showing the adapter connected to both a catheter and the prior art hypodermic syringe.

DETAILED DESCRIPTION OF THE PREFERRED EMBODIMENT

Figure 1:
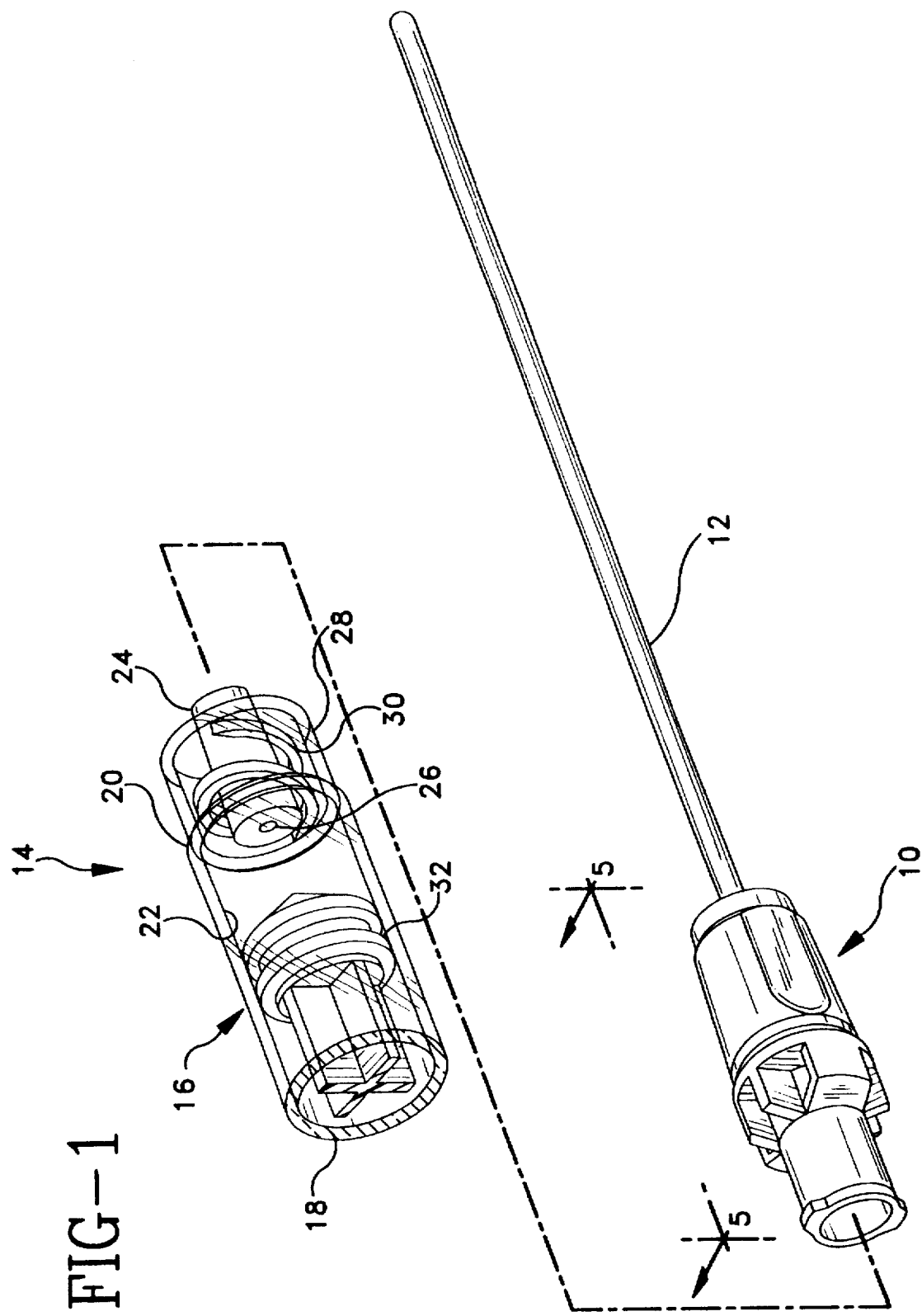
FIG. 1 is an exploded perspective view of the adapter and a portion of a prior art hypodermic syringe.
Figure 2:
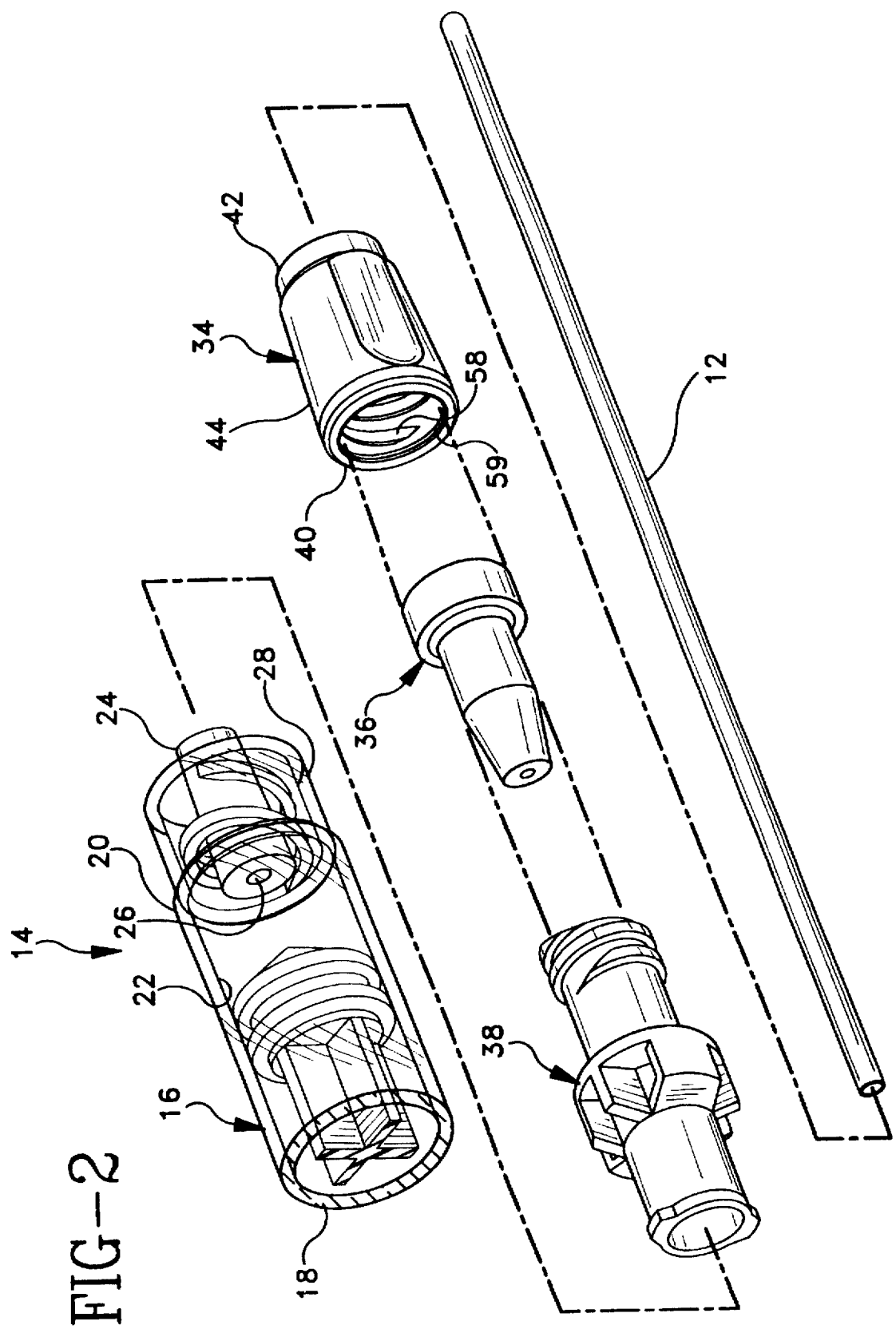
FIG. 2 is an exploded perspective view similar to FIG. 1, but showing the adapter in an exploded condition.

An adapter in accordance with the subject invention is identified generally by the numeral 10 in FIG. 1. Adapter 10 is used to place a flexible catheter 12 in communication with a fluid reservoir. As shown in FIGS. 1 and 2, the reservoir is a syringe 14. Syringe 14 includes a barrel 16 having an open proximal end 18, a partly closed distal end 20 and a fluid receiving chamber 22 therebetween. A tip 24 projects distally from distal end 20 of syringe barrel 16 and includes a narrow passage 26 extending axially therethrough and communicating with chamber 22 of barrel 16. A luer collar 28 concentrically surrounds tip 24 and includes an array of internal threads 30 for threaded engagement with adapter 10, as explained further herein. A plunger 32 is slidably disposed within chamber 22 and is operative to urge fluid through passage 26 of tip 24 into or out of chamber 22. With reference to FIG. 2, adapter 10 includes a nose 34, a plug 36 and a hub 38.

Figure 3:
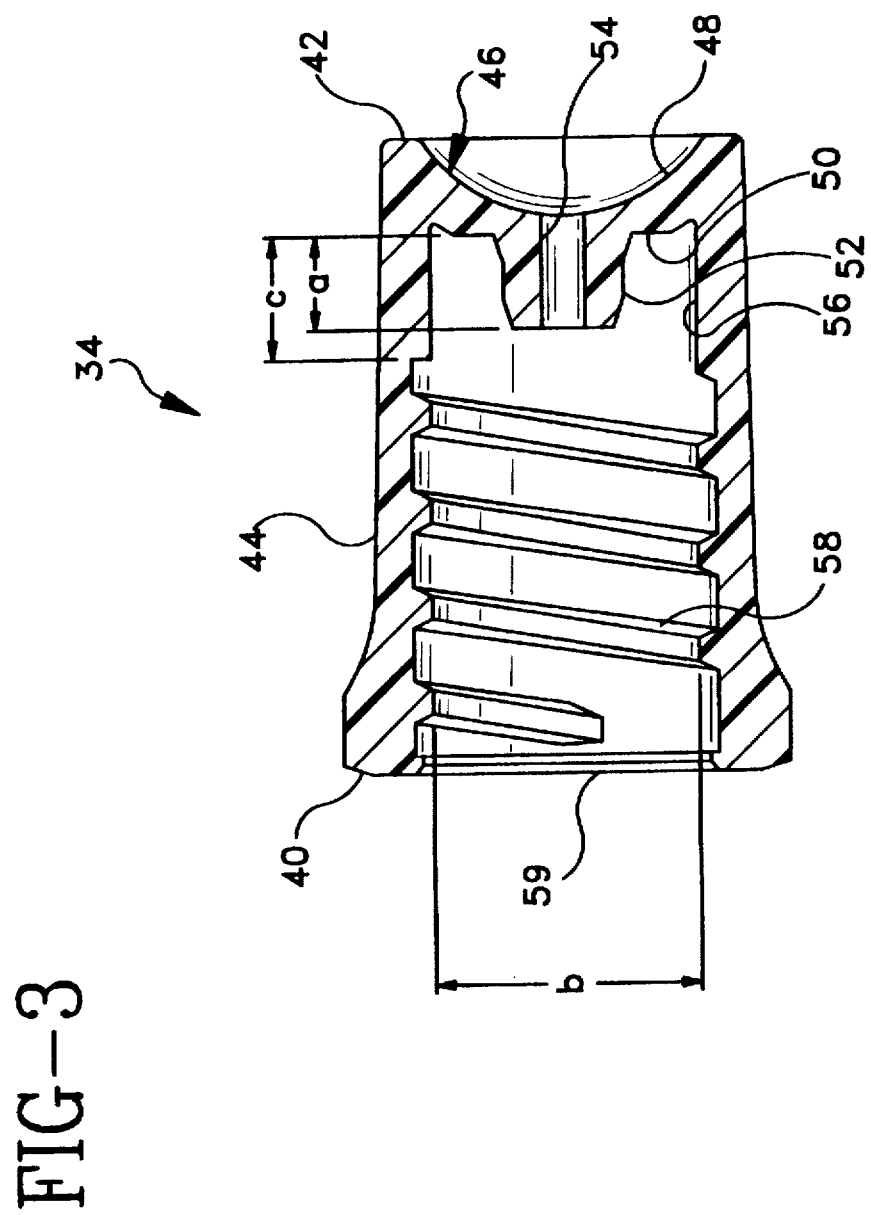
FIG. 3 is a cross-sectional view of the nose of the adapter assembly.

Nose 34, as shown most clearly in FIG. 3, is unitarily molded from a rigid plastic and includes a proximal end 40, a distal end 42 and a tubular side wall 44 extending therebetween. Distal end 42 includes an inwardly extending wall 46 having a concavely dished distal face 48 and a proximal face 50. A projection 52 extends from distal wall 46 proximally a distance "a" and is concentric with tubular side wall 44. An aperture 54 extends axially through distal wall 46 and projection 52, and is dimensioned to slidably receive catheter 12.

Tubular side wall 44 of nose 34 includes an inner cylindrical surface 56 concentrically surrounding projection 52 and defining an inside diameter "b". Inner cylindrical surface 56 projects proximally from face 50 of distal wall 46 a distance "c" which exceeds the axial length "a" of projection 52.

Tubular wall 44 further includes an array of internal threads 58 extending from inner cylindrical surface 56 toward proximal end 40. An annular locking rim 59 extends inwardly at proximal end 40.

As shown most clearly in FIGS. 1 and 2, outer surface regions of tubular wall 44 are non-cylindrical to facilitate digital manipulation and rotation of nose 34, as explained further herein.

Figure 4:
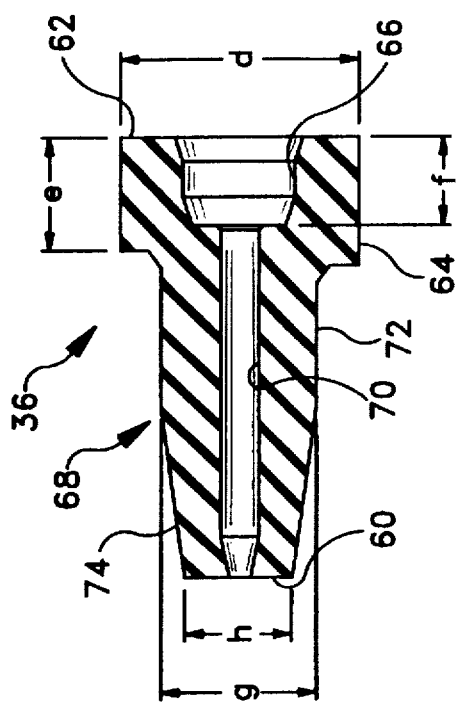
FIG. 4 is a cross-sectional view of the plug of the adapter assembly.

Plug 36 of adapter 10 is unitarily molded from a compressible elastomeric material, and includes opposed a proximal and distal ends 60 and 62, as shown in FIG. 4. Portions of plug 36 adjacent distal end 62 define a cylindrical flange 64 having an outside diameter "d" substantially equal to or slightly greater than the inside diameter "b" of inner cylindrical surface 56 on nose 34. Cylindrical flange 64 of plug 36 further defines an axial length "e" substantially equal to axial length "c" of inner cylindrical surface 56 on nose 34. Distal end 62 is characterized by a cavity 66 concentric with cylindrical flange 64 and defining a length "f" conforming to length "a" of projection 52 on nose 34. Additionally, the cross-sectional shape and dimensions of cavity 66 conform to or are slightly less than the corresponding cross-sectional dimensions of projection 52 on nose 34. With these relative dimensions, distal end 62 of plug 36 can be urged in a proximal-to-distal direction into open proximal end 40 of nose 34 and into fluid-tight engagement with interior portions of nose 34. In particular, outer surface regions of cylindrical flange 64 of plug 36 can be urged into fluid-tight engagement against inner cylindrical surface 56 of nose 34. Additionally, cavity 66 of plug 36 can be urged into fluid-tight engagement with projection 52 of nose 34.

Portions of plug 36 proximally of flange 64 define a catheter engagement section identified generally by the numeral 68. Catheter engagement section 68 includes a cylindrical catheter passage 70 extending axially therethrough from cavity 66 to proximal end 60 of plug 36. Portions of passage 70 extending proximally from cavity 66 define a diameter for closely receiving catheter 12 therein. However, a portion of passage 70 adjacent proximal end 60 of plug 36 is tapered inwardly to prevent catheter 12 from being urged entirely through passage 70.

Catheter engagement section 68 includes an outer cylindrical surface 72 proximally of flange 64 and an outer conically tapered surface 74 extending from cylindrical surface 72 to proximal end 60. Outer cylindrical surface 72 defines an outside diameter "g". Conical surface 74 tapers to a proximal end diameter "h".

Figure 5:
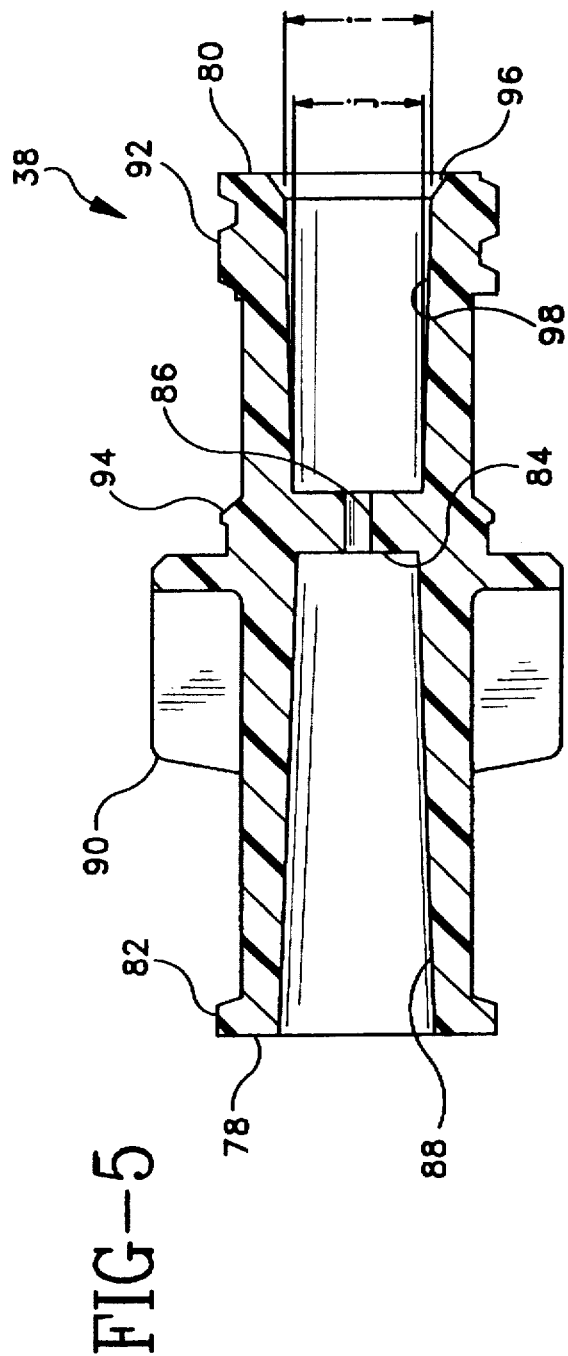
FIG. 5 is a cross-sectional view of the hub of the adapter assembly.

Hub 38 of adapter 10 is an elongate generally tubular member unitarily molded from a rigid plastic material. As shown in FIG. 5 hub 38 includes opposed proximal and distal ends 78 and 80 respectively. Proximal end 78 includes luer projections 82 dimensioned for threaded engagement with threads 30 of luer collar 28 on syringe 14. Hub 38 includes a wall 84 extending inwardly at a location intermediate proximal and distal ends 78 and 80. Wall 84 is characterized by an aperture 86 extending centrally therethrough and having a diameter substantially equal to the diameter of proximal portions of passage 70 through plug 36.

Portions of hub 38 between wall 84 and proximal end 78 define a tip receiving recess 88 dimensioned to nest over tip 24 of syringe barrel 14. Portions of hub 38 surrounding tip receiving recess 88 include fins 90 dimensioned to facilitate manual gripping and rotation of hub 38 relative to syringe barrel 14 and relative to nose 34, as explained further herein.

Hub 38 includes an array of external threads 92 extending proximally from distal end 80. External threads 92 on hub 38 are dimensioned for threaded engagement with internal threads 58 on nose 34. Hub 38 further includes a locking rim 94 dimensioned for snapped lock engagement with locking rim 59 on nose 34. Locking rim 94 includes a beveled distal face.

Hub 38 includes a chamfer 96 extending a short distance into distal end 80. Hub 38 further includes a tapered plug compression recess 98 extending from chamfer 96 to wall 84. Plug compression recess 96 is tapered to define smaller diameters closer to wall 84. In particular, a distal diameter "i" measured adjacent chamfer 96 is slightly less than diameter "g" of cylindrical surface 72 of plug 36. A minor diameter "j" measured adjacent wall 84 is slightly greater than diameter "h" of plug 36 adjacent proximal end 60.

Figure 6:
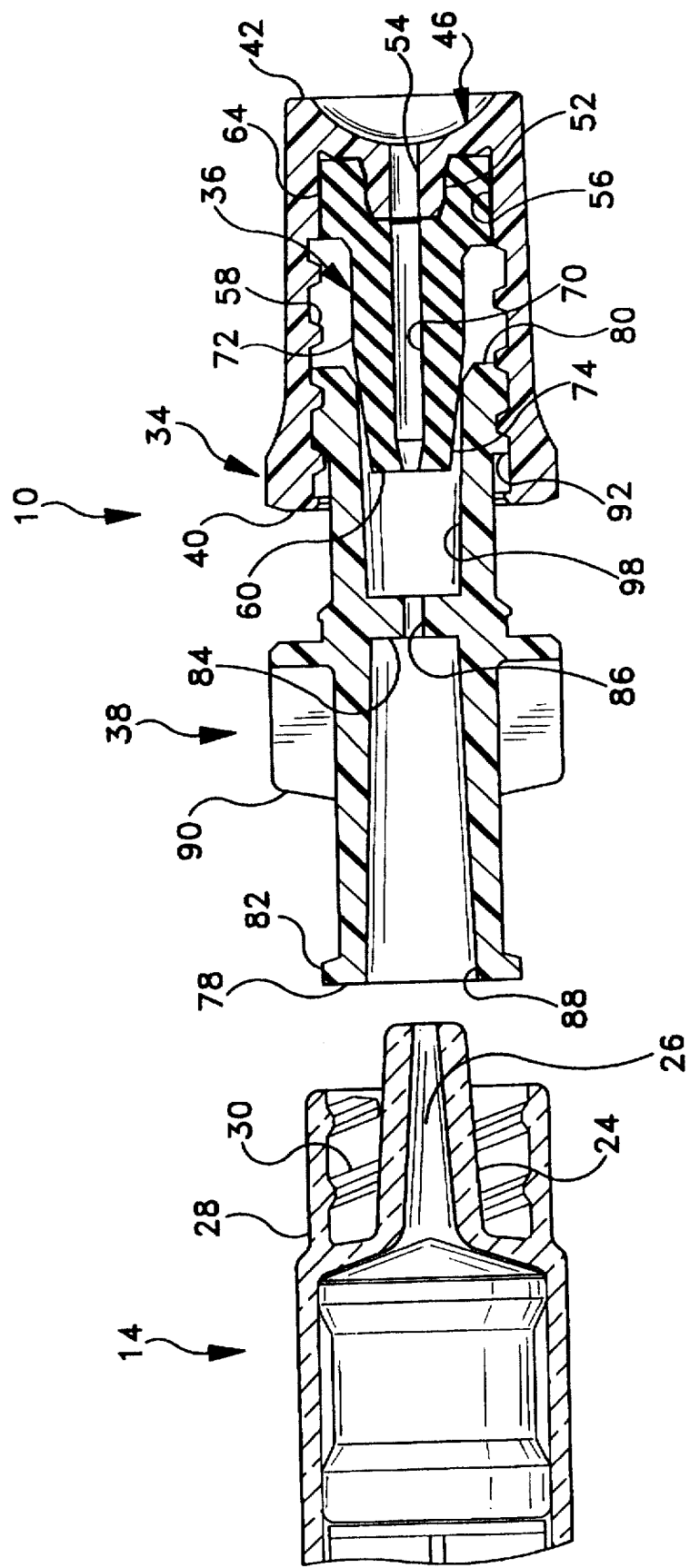
FIG. 6 is a cross-sectional view of the adapter and a prior art hypodermic syringe prior to connection of the adapter to a catheter.

Adapter 10 is used, as shown in FIGS. 6 and 7, by urging distal end 62 of plug 36 into open proximal end 40 of nose 34 such that distal end 62 of plug 36 seats against proximal face 50 of wall 46 on nose 34. In this engaged position, cavity 66 in distal end 62 of plug 36 is in fluid-tight engagement over projection 52 of nose 34. Additionally, the outer cylindrical surface of flange 64 seats tightly against inner cylindrical surface 56 of nose 34. The resiliency of plug 36 will prevent inadvertent separation of plug 36 from nose 34. In this assembled condition, passage 70 through plug 36 aligns axially with aperture 54 through nose 34.

Catheter 12 then is inserted through aperture 54 in distal wall 46 of nose 34 and into passage 70 of plug 36. Proximal movement of catheter 12 is stopped by tapered portions of passage 70 adjacent proximal end 60 of plug 36. Initial insertion of catheter 12 into passage 54 of nose 34 is facilitated by the dished concave configuration of distal surface 48 of wall 46.

Assembly of adapter 10 proceeds by threadedly engaging distal end 80 of hub 38 into open proximal end 40 of nose 34. More particularly, external threads 92 of hub 38 threadedly engage internal threads 58 of nose 34. Plug compression cavity 98 of hub 38 will telescope over conically tapered surface 74 of catheter engaging section 68 of plug 36. However, after sufficient threaded advancement, hub 38 will engage portions of conically tapered surface 74 of plug 36 adjacent cylindrical surface 72 thereof. Thus, further threaded advancement will cause tapered plug compression cavity 98 to gradually compress catheter engaging section 68 of plug 36. It will also be appreciated that advancement of hub 38 will cause tapered plug compression cavity 98 to transmit torsional forces upon catheter engaging section 68 of plug 36. Owing to the shapes of the compression cavity and catheter engaging section, the compressional and torsional forces exerted by the compression cavity upon the catheter engaging section are substantially uniform.

The gradual, uniform compression of and torsion applied to plug 36 will exert gripping forces on catheter 12, but, due to the tapers of mating surface 72 and 98, will not exert sufficient forces to cause occlusion or kinking of portions of catheter 12 within plug 36. Further tightening of hub 38 into nose 34 will cause locking rim 94 of hub 38 to engage locking rim 59 of nose 34. The tapered distal face of locking rim 94 will cause a slight outward expansion of the extreme proximal end 40 of nose 34 such that locking rim 94 will pass distally beyond locking rim 59 of nose 34. Further threaded movement will cause distal end 40 of nose 34 to resiliently return toward an undeflected condition such that locking rim 59 will resiliently engage over locking rim 94 of hub 38. In this locked A condition, as shown most clearly in FIG. 7 proximal end 80 of hub 38 will be substantially adjacent flange 64 of plug 36. Furthermore, owing to the gradual compressive and torsional forces exerted by plug compression cavity 98, plug 36 will have been evenly compressed at catheter engaging section 68 for efficient fluid-tight gripping of catheter 12.

Adapter assembly 10 and catheter 12 may be threadedly engaged with syringe 14. In particular, luer collar 28 of syringe 14 may be threaded onto luer projections 82 at proximal end 78 of hub 38 such that fluid receiving chamber 22 defined within barrel 16 of syringe 14 can be placed in fluid communication with catheter 12.

What is claimed is:

1. An adapter assembly for fluid-tight connection to a catheter, said assembly comprising:

a tubular nose have proximal and distal ends;

a resilient elastomeric plug having proximal and distal ends, said distal end of said plug being tightly engaged in said distal end of said nose, said proximal end of said plug being tapered, a catheter passage extending through said plug and being dimensioned for slidable engagement of said catheter therein; and a generally tubular hub having proximal and distal ends, said distal end of said hub being selectively movable in proximal and distal directions in said nose, a plug compression cavity extending into said distal end of said hub and receiving said proximal end of said plug, said plug having sufficient resiliency and said plug compression cavity being tapered and dimensioned such that distal movement of said hub into said nose causes said hub to gradually compress said plug into secure fluid-tight engagement with said catheter.

2. The adapter assembly of claim 1, wherein said nose comprises an array of internal threads, and wherein said hub comprises an array of external threads, said internal and external threads being engageable for the selective movement of the hub in the nose.

3. The adapter assembly of claim 2, further comprising a locking rim on said nose and a locking rim on said hub, said locking rims being releasably engageable with one another when said threads are fully tightened.

4. The adapter assembly of claim 1, comprising a locking rim on said nose and a mateable locking rim on said hub, said locking rims being dimensioned and configured for snap engagement with one another.

5. The adapter assembly of claim 1, wherein said plug comprises a generally cylindrical surface distally of and adjacent the tapered proximal end of said plug.

6. The adapter assembly of claim 5, wherein said hub includes a chamfer at said distal end, said plug compression cavity being disposed proximally of and adjacent said chamfer, said plug compression cavity defining a distal diameter adjacent said chamfer, said distal diameter being less than a diameter defined by said cylindrical surface of said plug.

7. The adapter assembly of claim 6, wherein the plug compression cavity defines a proximal diameter greater than a diametrical dimension of said plug at said proximal end thereof.

8. The adapter assembly of claim 1, wherein said nose includes a distal wall extending inwardly at said distal end of said tubular side wall, a projection extending proximally from said distal wall of said nose, an aperture extending through said distal wall and through said projection, said distal end of said plug having a recess formed therein and configured for fluid-tight engagement over said projection of said nose.

9. The adapter assembly of claim 1, wherein portions of the catheter passage adjacent said proximal end of said plug are tapered for preventing complete passage of said catheter through said plug.

10. The adapter assembly of claim 1, wherein said hub includes an inwardly extending wall intermediate said proximal and distal ends thereof, said wall being disposed for engaging said proximal end of said plug and including an aperture extending therethrough and aligned with said catheter passage of said plug.

11. The adapter assembly of claim 1, wherein said proximal end of said hub including luer projections for threaded engagement with a luer collar.

12. The adapter assembly of claim 1, wherein outer surface portions of said hub include fins formed thereon for facilitating digital manipulation and rotation of said hub.

* * * * *